United States Patent [19]

Tang et al.

[11] 4,296,244
[45] Oct. 20, 1981

[54] (3-TRIFLUOROMETHYLPHENYL)-ALPHA-HYDROXYACETIC ACID AND PROCESS FOR PREPARATION

[75] Inventors: David Y. Tang, Eggertsville; Arthur M. Foster, Snyder, both of N.Y.

[73] Assignee: Hooker Chemicals & Plastics Corp., Niagara Falls, N.Y.

[21] Appl. No.: 92,118

[22] Filed: Nov. 7, 1979

[51] Int. Cl.³ ............................................. C07C 59/84
[52] U.S. Cl. .............................. 562/470; 260/545 R; 560/105; 562/459
[58] Field of Search ......................................... 562/470

[56] References Cited

U.S. PATENT DOCUMENTS 3,729,305  4/1973  Dovan .................................. 562/496
4,186,270  1/1980  Dowd et al. ......................... 562/496

FOREIGN PATENT DOCUMENTS 2444194  4/1975  Fed. Rep. of Germany ...... 562/470
1095035  8/1976  Japan ................................... 562/496
2012143  1/1977  Japan ................................... 562/496

Primary Examiner—Paul J. Killos
Attorney, Agent, or Firm—William J. Crossetta, Jr.; Arthur S. Cookfair

[57] ABSTRACT

The present invention provides a novel organic compound, (3-trifluoromethylphenyl)-alpha-hydroxyacetic acid, and a process for the preparation thereof comprising the steps of:

a. converting (3-trifluoromethyl)-benzotrichloride to the corresponding benzoyl chloride,
b. cyanation of the benzoyl chloride to produce the corresponding benzoyl cyanide,
c. hydrolyzing the benzoyl cyanide to produce the corresponding keto-acid, and
d. hydrogenating the keto-acid to produce (3-trifluoromethylphenyl)-alpha-hydroxyacetic acid.

6 Claims, No Drawings

(3-TRIFLUOROMETHYLPHENYL)-ALPHA-HYDROXYACETIC ACID AND PROCESS FOR PREPARATION

The present invention relates to (3-trifluoromethylphenyl)-alpha-hydroxyacetic acid and to its production

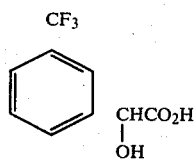

(3-trifluoromethylphenyl)-alpha-hydroxyacetic acid is useful as a chemical intermediate in the production of methyl and ethyl esters of (3-trifluoromethylphenyl)-acetic acid.

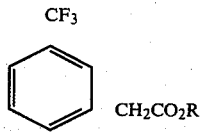

wherein R=CH$_3$ or C$_2$H$_5$

Methyl and ethyl esters of (3-trifluoromethylphenyl)-acetic acid are intermediates useful to produce 3-phenyl-4-piperidinones, such as 1-methyl-3-phenyl-5-[3-trifluoromethylphenyl]-4(1H)-pyridinone and 2-methyl-4-trifluoroolyl isoxazolinone.

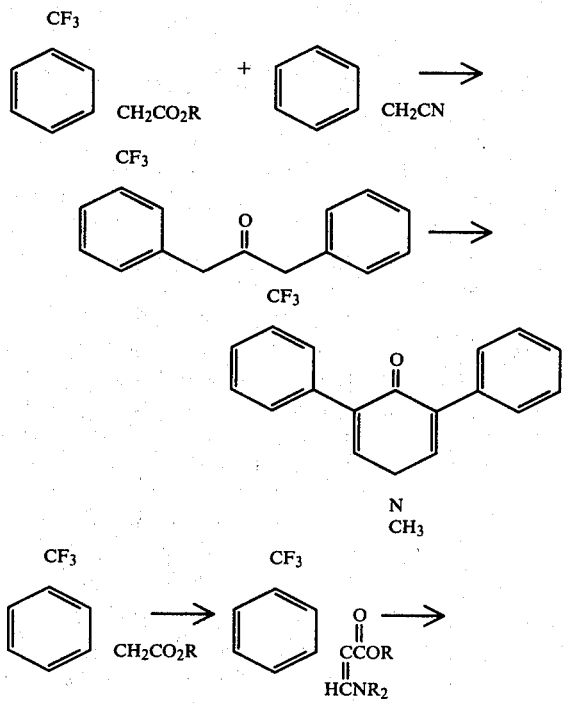

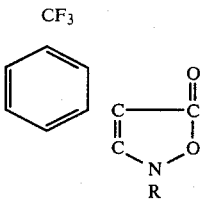

3-phenyl-4-piperidinones are useful herbicides, especially for the preemergent control of foxtail and bindweed. Examples of such piperidinones and their herbicidal properties are described in detail in German Offenlegungsschrift No. 2,537,753 (Mar. 11, 1978) and in German Offenlegungsschrift No. 2,628,992 (Jan. 20, 1977).

BRIEF DESCRIPTION OF THE INVENTION

The present invention relates to a novel organic compound, (3-trifluoromethylphenyl)-alpha-hydroxyacetic acid. This compound may be produced by:

a. converting (3-trifluoromethyl)-benzotrichloride to the corresponding benzoyl chloride, b. cyanation of the benzoyl chloride to produce the corresponding benzoyl cyanide, c. hydrolyzing the benzoyl cyanide to produce the corresponding keto-acid, d. hydrogenating the keto-acid to produce (3-trifluoromethylphenyl)-alpha-hydroxyacetic acid, The present compound is useful as an intermediate a produce methyl and ethyl esters of (3-trifluoromethylphenyl)-acetic acid. Methyl and ethyl esters of (3-trifluoromethylphenyl)-acetic acid may be produced utilizing (3-trifluoromethylphenyl)alpha-hydroxyacetic acid, the product of (d), by the following steps:

e. hydrogenating (3-trifluoromethylphenyl)-alpha-hydroxyacetic acid in the presence of glacial acetic acid to produce the corresponding substituted acetic acid, and f. esterifying the substituted acetic acid using an alcohol selected from the group consisting of methyl and ethyl to obtain the corresponding methyl or ethyl ester of (3-trifluoromethylphenyl)-acetic acid.

With reference to step (a), the reaction is carried out at a temperature between about 120° and about 130° C. in the presence of a catalyst, such as ferric chloride. The required, stoichiometric amount, of water is slowly added to the catalyst-reactant mixture. The product may suitably be recovered by distillation. The product was confirmed by spectral analysis to be (3-trifluoromethyl)-benzoyl chloride.

With reference to step (b), the cyanation step is suitably carried out at temperatures between about 170° and about 200° C. and, more preferably, between about 180° and about 190° C. using a cyanide source, such as sodium, potassium or cuprous cyanide. The reaction is carried out over a period of from about 2 to about 8 hours. Typically, about 6 hours is required to complete the reaction. The product may suitably be recovered by distillation. The product, identified by NMR, IR and GPC analyses, was (3-trifluoromethyl)-benzoyl cyanide.

With reference to step (c), the hydrolysis is suitably carried out in concentrated hydrochloric acid at ambient temperatures. A colorless, needle-like crystalline product, recovered by filtration, was confirmed by NMR and IR analyses to be (3-trifluoromethylphenyl)-glyoxylic acid.

With reference to step (d), the keto-acid product of step (c). is hydrogenated, suitably utilizing a known hydrogenation catalyst, such as palladium, and a solvent, such as ethanol or ethyl acetate, to produce a white solid product, (3-trifluoromethylphenyl)-alpha-hydroxyacetic acid. The structure of the product was confirmed by NMR and IR analyses.

With reference to step (e), the product of step (d), (3-trifluoromethyphenyl)-alpha-hydroxyacetic acid, is hydrogenated using a hydrogenation catalyst, such as palladium, in the presence of glacial acetic acid to produce the corresponding substituted acetic acid, (3-trifluoromethylphenyl)-acetic acid.

With reference to step (f), the substituted acetic acid product of step (e) was esterified by simple esterification with methyl or ethyl alcohol to produce the corresponding methyl or ethyl ester of (3-trifluoromethylphenyl)-acetic acid.

DETAILED DESCRIPTION OF THE INVENTION

Examples 1, 2, 3 and 4 illustrate the production of (3-trifluoromethylphenyl)alpha-hydroxyacetic acid. Examples 5 and 6 illustrate the use of (3-trifluoromethylphenyl)alpha-hydroxyacetic acid to produce methyl and ethyl esters of (3-trifluoromethylphenyl)acetic acid.

EXAMPLE 1

CONVERSION

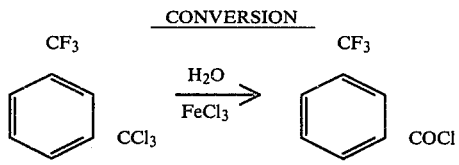

A mixture of 44.2 grams (0.168 mol) of (3-trifluoromethyl)-benzotrichloride and 0.14 gram (0.3% by weight) of ferric chloride were stirred together and 3.0 grams (0.168 mol) of water was added drop-wise while the temperature of the mixture was maintained between about 120° and about 130° C. After the addition, the mixture was stirred for one-half hour. A dark mixture formed and was subsequently distilled at a reduced pressure to recover 30.5 grams (about 87% yield) of a colorless liquid product. By spectral analysis the product was confirmed to be (3-trifluoromethyl)-benzoyl chloride. The recovered product was found to be eminently suited for use in the subsequent process steps without further treatment.

EXAMPLE 2

CYANATION

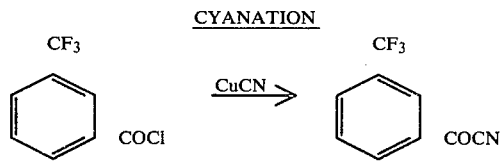

28.4 grams (0.127 mol) of the product of Example 1 and 18.2 grams (0.2 mol) of cuprous cyanide were charged into a round-bottomed flask. The mixture was heated to a temperature between about 185° and about 190° C. for a period of six hours. The product was recovered from the reaction mixture by distillation under reduced pressure. 22.4 grams (88% yield) of a white liquid product was recovered. The product was found to have a boiling point between about 135° and about 138° C. The structure of the product was confirmed by $^{13}C$ NMR, IR and GPC analyses to be (3-trifluoromethyl)-benzoyl cyanide. The product was found to be suited to use in the following process steps without further treatment.

EXAMPLE 3

HYDROLYSIS

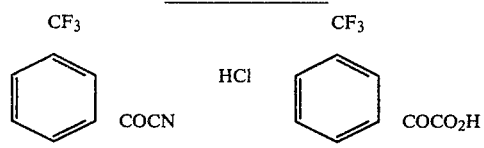

A mixture of 5.0 grams (0.025 mol) of (3-trifluoromethyl)-benzoyl cyanide in 40 ml of concentrated hydrochloric acid was stirred vigorously at room temperature. After five hours, a white solid gradually formed and precipitated out. The solution was allowed to stand overnight and then filtered. The white solid was washed with water and recrystallized from ether-hexane to afford 3 grams (about 61% yield) of a colorless needle-like crystalline product. The product was confirmed to be (3-trifluoromethylphenyl)-glyoxylic acid, or in alternative nomenclature, (3-trifluoromethyl)-benzoyl formic acid, by $^{13}C$ NMR and IR analyses. Without further treatment the product was suited to use in the following process steps.

EXAMPLE 4

FIRST HYDROGENATION

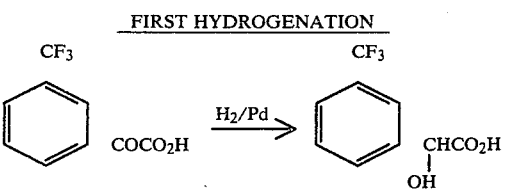

A mixture of 40 ml of ethanol, 0.4 grams of a 5% palladium catalyst on a carbon carrier and 1.0 gram of concentrated sulfuric acid were stirred and 2.2 grams (0.01 mol) of (3-trifluoromethylphenyl)-glyoxylic acid was added. The mixture was then transferred into a Parr hydrogenator and hydrogenated under 30 psig of hydrogen at ambient temperature for a period of one hour. The hydrogenated mixture was filtered, concentrated in a rotary evaporator to remove any remaining ethanol, diluted with water and extracted with ether. The resultant product was dried over a bed of magnesium sulfate and subsequently concentrated to yield 0.9 gram of a white solid product having a melting point between about 95° and about 100° C. The structure of the product was confirmed by $^{13}C$ NMR, $^1H$ NMR and IR analyses to be (3-trifluoromethylphenyl)-alpha-hydroxyacetic acid. The product without further treatment was found to be suited to use in the following process steps.

EXAMPLE 5

SECOND HYDROGENATION

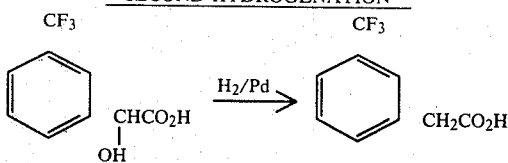

0.5 grams of concentrated sulfuric acid was added to a mixture of 1.7 grams (7.9 mol) of (3-trifluoromethylphenyl)-alpha-hydroxyacetic acid, the product of Example 4, in 20 ml of glacial acetic acid and 0.2 gram of 5% palladium on a carbon base. The resultant mixture was hydrogenated in a Parr hydrogenator under 45 psig of hydrogen for a period of four hours. The mixture was then filtered, concentrated, diluted with water and subsequently extracted with ether. The organic layer was then dried and concentrated to produce 1.15 gram (72% yield) of a white solid. The structure of the product was confirmed by NMR and IR analyses to be (3-trifluoromethylphenyl)-acetic acid. The product without further treatment was suited to use in the following step.

EXAMPLE 6

ESTERIFICATION

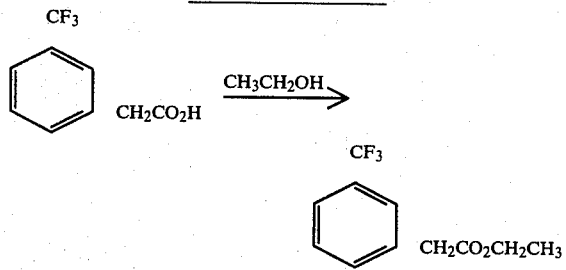

15.3 grams (0.075 mol) of the product of Example 5, 0.5 ml of concentrated sulfuric acid and 90 ml of absolute ethanol were charged into a flask. The flask was fitted with a Soxhlet column with 16 grams of 3 A molecular sieves in the filter tube. The mixture was refluxed with stirring for a period of 20 hours. 1 gram of sodium carbonate was then added to neutralize the acid. The mixture was then filtered and the ethanolic solution recovered and concentrated. The resultant residue was then distilled under reduced pressure to afford 16.3 gram (94% of theoretical yield) of the ethyl ester of (3-trifluoromethylphenyl)-acetic acid. The structure of the product was confirmed by NMR, IR and GPC analyses.

The methyl ester may be prepared in a like manner utilizing methanol in place of ethanol in the foregoing example.

The foregoing description and embodiments are intended to illustrate the invention without limiting it thereby. It will be understood that various modifications can be made in the invention without departing from the spirit or scope thereof.

What is claimed is:

1. (3-trifluoromethylphenyl)-alpha-hydroxyacetic acid.

2. A process of producing (3-trifluoromethylphenyl)-alpha-hydroxyacetic acid comprising the steps of:
   (a) reacting (3-trifluoromethyl)-benzotrichloride with water to form the corresponding benzoyl chloride,
   (b) cyanation of the benzoyl chloride by reaction with CuCN to produce the corresponding benzoyl cyanide,
   (c) hydrolyzing the benzoyl cyanide to produce the corresponding keto-acid,
   (d) hydrogenating the keto-acid in the presence of an hydrogenation catalyst to produce (3-trifluoromethylphenyl)-alpha-hydroxyacetic acid.

3. The process of claim 2 wherein step (a) is carried out at temperatures between about 120° and about 130° C.

4. The process of claim 2 wherein step (a) is catalyzed and the catalyst is ferric chloride.

5. The process of claim 2 wherein step (b) is carried out at temperatures between about 170° and about 200° C.

6. The process of claim 2 wherein step (c) is carried out in the presence of concentrated hydrochloric acid.

* * * * *